United States Patent
Zou et al.

(10) Patent No.: US 8,202,904 B2
(45) Date of Patent: Jun. 19, 2012

(54) α-CYANO-4-FLUORO-3-PHENOXYBENZYL META-HALO PYRETHRATE, A PROCESS FOR PREPARING THE SAME AND THE USES THEREOF

(75) Inventors: Xinzhuo Zou, Shanghai (CN); Shuxv Gao, Shanghai (CN); Huihua Cai, Shanghai (CN)

(73) Assignee: East China Normal University, Shanghai (CN)

( * ) Notice: Subject to any disclaimer, the term of this patent is extended or adjusted under 35 U.S.C. 154(b) by 173 days.

(21) Appl. No.: 12/671,886

(22) PCT Filed: Jul. 10, 2008

(86) PCT No.: PCT/CN2008/071600
§ 371 (c)(1),
(2), (4) Date: Jul. 29, 2010

(87) PCT Pub. No.: WO2009/018740
PCT Pub. Date: Feb. 12, 2009

(65) Prior Publication Data
US 2010/0286265 A1 Nov. 11, 2010

(30) Foreign Application Priority Data
Aug. 3, 2007 (CN) .......................... 2007 1 0044542

(51) Int. Cl.
A01N 53/08 (2006.01)
C07C 255/39 (2006.01)

(52) U.S. Cl. ........................................ 514/521; 558/407
(58) Field of Classification Search .................. 514/521; 558/407
See application file for complete search history.

(56) References Cited

U.S. PATENT DOCUMENTS 5,004,822 A    4/1991  Elliott et al.

FOREIGN PATENT DOCUMENTS

| | | |
|---|---|---|
| CN | 1044650 | 8/1990 |
| CN | 1508124 | 6/2004 |
| DE | 2326077 | 1/1974 |
| EP | 0381563 | 8/1990 |
| FR | 2185612 | 1/1974 |

OTHER PUBLICATIONS

International Search Report of PCT/CN2008/071600, dated Oct. 16, 2008.
Shan et al., "Primary study of pyrethroid pesticide used in paddy field," Pesticide Science and Administration, 2000, 21(5), pp. 21-23 (with English language abstract thereof).
Li et al., "The development strategy of the 21 century organic chemistry," Chemical Industry Press, 2002, p. 371-380.
Ren et al., "An introduction of endocrine disrupters (EDCs)", Safety and Environmental Engineering, 2004, vol. 11, No. 3, 4 pages total (with English language abstract thereof).
Zheng et al., "Development of deltamethrin toxicity and mutagenicity," Journal of Beijing Agricultural College, 2004, vol. 19, No. 1, pp. 77-80 (with English language abstract thereof).
Zhang et al., "The assay of toxicity of insecticides," The Science Press, 1988, pp. 88-92 (with English language abstract thereof).
Zhang et al., "Syntheses of 2(3)-fluoro-4-methoxymethylbenzyl and 2(3)-fluoro-4-methybenzyl ester of pyrethric acid and their insecticidal activity," Chinese Journal of Organic Chemistry, 2005, vol. 25, No. 8, pp. 991-993 (with English language abstract thereof).
Zeng et al., "Comparison of biochemical characterization of carboxylesterase in susceptible and resistant strains of German cockroach, *Blatella germanica*," Chin J Vector Bio & Control, 2004, vol. 15, No. 2, pp. 4 pages total(with English language abstract thereof).
Elliott et al., "The pyrethrins and related compounds, part XXX$^\alpha$: esters from acids with mono-halovinyl side chains," Pestic. Sci., 1986, pp. 708-714.
Elliott et al., "Synthetic insecticide with a new order of activity," Nature, vol. 248, 1974, pp. 710-711.

*Primary Examiner* — Kamal Saeed
*Assistant Examiner* — Kristin Bianchi
(74) *Attorney, Agent, or Firm* — Hamre, Schumann, Mueller & Larson, P.C.

(57) ABSTRACT

The present invention relates to a compound of formula (I), stereoisomers thereof or the mixture of these stereoisomers, wherein: X represents a halogen atom, i.e. F, Cl, Br. The present invention also relates to a process for preparing the compound, and to a use of the compound in the preparation of an insecticide for controlling or killing vectors in the public hygiene and disease control, and to a use of the compound in the preparation of an insecticide for controlling or killing insects, nematodes, and mites in agriculture or horticulture.

(I)

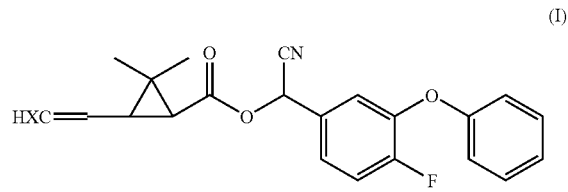

12 Claims, No Drawings

α-CYANO-4-FLUORO-3-PHENOXYBENZYL META-HALO PYRETHRATE, A PROCESS FOR PREPARING THE SAME AND THE USES THEREOF

TECHNICAL FIELD

The present application relates to a pesticide field, more particularly, to a type of novel pyrethroid insecticides: α-cyano-4-fluoro-3-phenoxy benzyl meta-halo pyrethrate, and the present invention also relates to a process for preparing the same, and to the uses thereof.

BACKGROUND

Pyrethroid insecticide is a kind of biomimetic pesticide with high efficiency, wide insecticidal spectrum, low toxicity and safe to humans and animals. It thus has been widely used and has become one of the major products of insecticides. The primary pyrethric acid series, such as allethrin, tetramethrin, phenothrin, furamethrin, and the analogues, play an important role in public hygiene as well as in controlling vector insects; the development of dihalopyrethroids with high efficiency and low toxicity, such as Cypermethrin (M. Elliott et al., Ger. P2326077, 1974), Deltamethrin (M. Elliott et al., Nature, 248, 1974, 710), and the analogues, is a milestone in the history of pesticides, and the presence of two chlorines atoms on the double bond makes pyrethroids to possess better light stability in comparison with chrysanthemumate pertaining to the primary pyrethric acid series and thus has been widely used in the protection of agriculture plants.

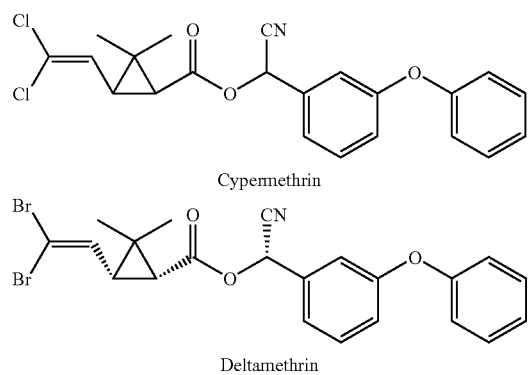

Deltamethrin is particularly valuble, which was synthesized by Elliott in 1974 based on the study of the chemical structures of natural pyrethrins. It is a type II α-cyano-containing pyrethroids class bionic pesticide, and is one of the most efficient synthetic pyrethroid insecticides. It possesses the following features: being used in a small amount, stable to light, metabolized and excreted in mammals quickly, having broad-spectrum and low-residue, effective to insects which is resistant to organic phosphorus, and mainly used to control the agricultural insects in cotton fields, vegetable plots, fruit trees and tea, as well as hygiene insects, used in fisheries production for killing parasites as well. Therefore, it is one of the flagship products of pesticides in the world, with annual sales of more than 250 million U.S. dollars. However, since they have been used for a long term, pyrethroid insecticides are facing a fatal problem, i.e. insects have become severely resistant to them (edited by Zhengming L I, Huazheng YANG; Canping D U, Lusheng L I U, Heng ZHANG, "The development strategy of the 21 century Organic Chemistry", Chemical Industry Press, Beijing, 2002, p371-380.). The severe resistance to Cypermethrin, Deltamethrin, and Fenvalerate which are used mainly in agriculture was reported successively in the 1980s and affected their persistent uses (Zhengjun SHAN, Zhonglin Z H U et al. Pesticide Science and Administration, 2000, 21(5), 22). Pyrethroids used in hygiene, such as allethrin, tetramethrin, and the like, are also facing the same problem. (Xiaopeng C A O, Caihong Y U, Xiwu G A O, Chinese vector Biology and Control journal, 2004, 15(2), 105). For example, dengue fever and encephalitis prevailed in Taiwan, Hong Kong, Guangdong, Fujian and other areas in recent years, and it was reported that the resistance of the local mosquitoes to pyrethroid insecticides was the root causes for these diseases. Moreover, this problem has a trend of continued spreading. In order to deal with the insects, such as mosquitoes which is more and more difficult to kill, producers have to keep on increasing the pesticides' concentration, and the trump pesticide, Deltamethrin with moderate toxicity (the acute toxicity for rat by oral administration LD50 70~140 mg/kg), which used to be only applied for agriculture, is now also used in the home. However, this will lead to a more vicious cycle, further affecting its sustainable use. In the other aspect, the major product of pyrethroids, Deltamethrin, is recently under suspicion to have a teratogenicity and mutagenicity (Weihua ZHENG, Jianzhuang ZHAO, Deying M A, Shicong H O U, Transaction of Agriculture college of Beijing, 2004, 19(1), 77). Another major product of pyrethroids, Cypermethrin, is recently under suspicion to be an incretion interferent (i.e. an environmental hormone) and is listed by the US Our Stolen Future website (Ren REN, Jun HUANG, Safety and Environmental Engineering, 2004, 11(3), 7). It is believed to be an estrogen which can interfere the procreation function of humans and animals.

2,2-dimethyl-3-(2-chlorovinyl)cyclopropane carboxylate, 2,2-dimethyl-3-(2-bromovinyl)cyclopropane carboxylate, 2,2-dimethyl-3-(2-fluorovinyl)cyclopropane carboxylate, (referred to as meta-halo pyrethrate hereafter) such as α-cyano-3-phenoxybenzyl-2,2-dimethyl-3-(2-chlorovinyl)cyclopropane carboxylate, α-cyano-3-phenoxybenzyl-2,2-dimethyl-3-(2-bromovinyl)cyclopropane carboxylate, are only detected in minute quantities in the biodegradation or photodegradation products of Cypermethrin and Deltamethrin and have never been efficiently used. Elliott has synthesized and pointed out that the insecticidal activity of the following α-cyano-3-phenoxy benzyl meta-halo pyrethrate was lower than that of the corresponding α-cyano-3-phenoxy benzyl di-halo pyrethrate (Pestic. Sci. 17, 1986, 708.):

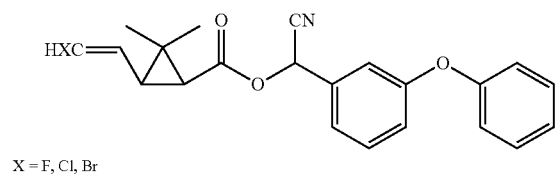

X = F, Cl, Br

Demassey, Jacques et al. has generally disclosed a compound with following formula in their patent application (CN1044650A, EP-381563):

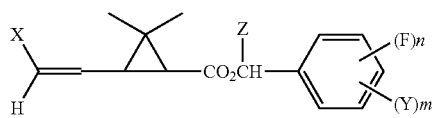

and this reference has specifically disclosed the following tetrafluorobenzyl meta-halo pyrethrate:

X = F, Cl, Br
Y = H, F, CH₃, CH₂OCH₃

However, all of these compounds have such low insecticidal activities that they can not meet the requirements on the pyrethroids in the public hygiene, in controlling vector insects and protecting agriculture plants. In addition, their alcohol part is polyfluorobenzyl alcohol, which is difficult to be synthesized and expensive. In fact, none of the meta-halo pyrethrate pyrethroids has been commercially produced.

In recent years, the factors, such as population growth, and the like, cause shortage in food, which further causes a global rise in foodstuff price; and, the global warming that expedites the propagation of harmful insects such as mosquitoes. It results in the spreading tendency of the infectious diseases, such as ague, dengue fever, and West Nile virus, which are spread by the mosquitoes. The survival of humans faces a new challenge, and human beings need more and better pesticides to guarantee the foodstuff production and people's health. In the other hand, a lot of attention has been paid to the food safety problem caused by residual pesticides. Therefore, the Europe Union, Japan and the other countries have adopted the most severe standard so far on the maximum residue limits for pesticides (MRL) in foods. For example, the MRL of fenvalerate in teas reduces from 0.1 mg/L in 1999 to 0.05 mg/L. Therefore, there is an urgent need to develop a novel pesticide with stability, high activity, quick efficiency, low resistance and liability to degradation.

CONTENTS OF THE INVENTION

The purpose of the present invention is to provide a type of novel pyrethroid insecticide having high activity and low residue, i.e. α-cyano-4-fluoro-3-phenoxybenzyl meta-halo pyrethrate, to overcome the deficiency of the prior art.

One purpose of the present invention is to provide the α-cyano-4-fluoro-3-phenoxybenzyl meta-halo pyrethrate.

Another purpose of the present invention is to provide a process for the preparation of the α-cyano-4-fluoro-3-phenoxybenzyl meta-halo pyrethrate.

Another purpose of the present invention is to provide a use of the α-cyano-4-fluoro3-phenoxybenzyl meta-halo pyrethrate as an insecticide.

After carefully analyzing the chemical structures of pyrethroids, we believe that the dihalopyrethroids having high efficiency and low toxicity, represented by Cypermethrin, and Deltamethrin, are excessively considered the light stability of double bond, thus causing the occurrence of overstability phenomena, the increase of the residual time in the environment, which is one of the most important reasons for teratogenicity, mutagenicity or becoming an incretion interferent. The light stability of meta-halo pyrethrate pyrethroids is slightly poorer than that of the structure bearing two halo atoms since it replaces one of the halo atoms with a hydrogen atom on the double bond, and meta-halo pyrethrate pyrethroids can be easily photodegraded or biodegraded, and can solve the overstability problem of the dihalopyrethroids having high efficiency and low toxicity, represented by Cypermethrin, and Deltamethrin. However, there is a need to improve the low insecticidal activity of this kind of pyrethrate. After uninterrupted efforts, the object of the present invention was achieved by the following technical solutions:

A compound of formula (I), stereoisomers thereof or the mixture of these stereoisomers is provided:

(I)

wherein: X represents a halogen atom, i.e. F, Cl, Br.

In particular, the compound is selected from:
α-cyano-3-phenoxy-4-fluoro-benzyl-2,2-dimethyl-3-(2-fluorovinyl)cyclopropane carboxylate,
α-cyano-3-phenoxy-4-fluoro-benzyl-2,2-dimethyl-3-(2-chlorovinyl)cyclopropane carboxylate, or
α-cyano-3-phenoxy-4-fluoro-benzyl-2,2-dimethyl-3-(2-bromovinyl)cyclopropane carboxylate.

This type of compounds have the advantages of high activity, low residue, high safety factor, simple structure, ease for synthesis, low cost and the like.

In the second aspect of the present application, it is provided a process for the preparation of the compound of formula (I) comprising:

(a) condensing the compound of formula (V) with 3-phenoxy-4-fluoro-benzaldehyde of formula (III) in the presence of an alkali metal cyanide by esterification reaction; or (b) esterificating the compound of formula (V) with α-cyano-3-phenoxy-4-fluoro-benzyl alcohol (IV) in the presence of a weak organic alkali, preferably pyridine.

(II)

X = F, Cl, Br (III)

(IV)

(V)

X = F, Cl, Br wherein the compound 3-phenoxy-4-fluoro-benzaldehyde (III) and the compound α-cyano-3-phenoxy-4-fluoro-benzyl alcohol (IV) are known and commercially available.

Meta-halo acid (II) can be synthesized by known methods (for example, Pestic. Sci. 17, 1986, 708.); the compound of formula (V) can be synthesized from meta-halo acid (II) and thionyl chloride by known methods (for example, Qiuxian ZHANG, Xia CHEN, Xinzhuo Z O U, "The synthesis of the secondary pyrethric acid mixed fluoro-containing benzyl ester and its insecticidal activity" Organic Chemistry, 2005, 25, 991).

In the third aspect of the present application, it is provided a new process for the synthesis of meta-halo acid (II):

FR patent 2185612 and CN1044650A proposed a method for preparing meta-halo acid (II) wherein X is chlorine or bromine from the corresponding t-butyl pyrethrate. The present application proposed a method for preparing meta-halo acid (II) from racemic or chiral, trans or cis-methylpyrethrate or the mixture thereof as an industry product directly via Witting reaction, as shown in Scheme 1 and Scheme 2. The details will be described in the experimental section.

Scheme 1. Synthetic route of meta-chloro pyrethric acid

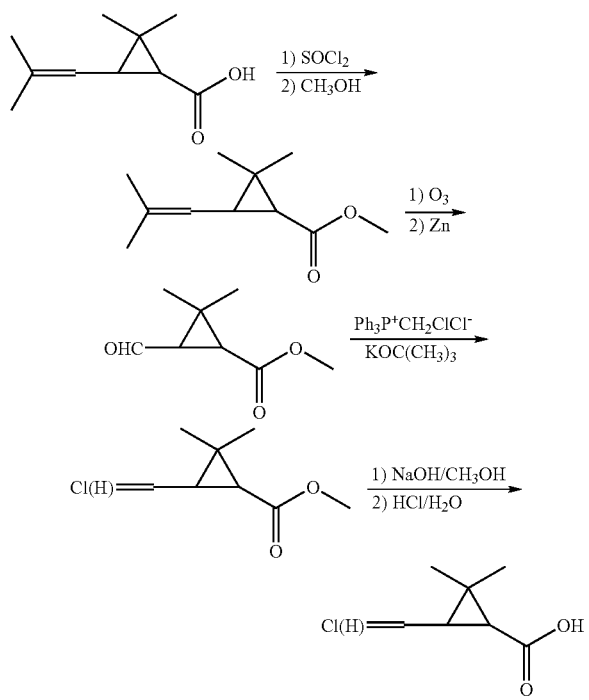

Scheme 2. Synthetic route of meta-bromo pyrethric acid

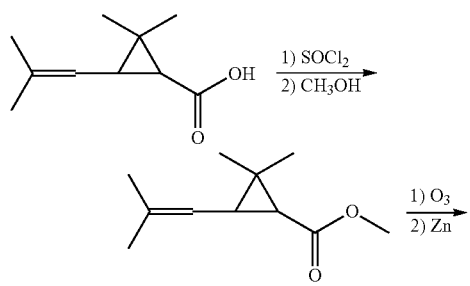

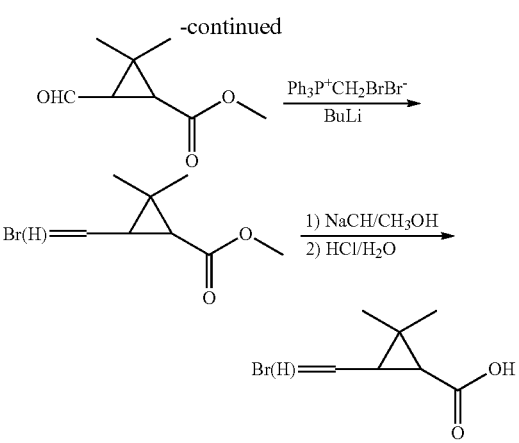

In the fourth aspect of the present application, it is provided a use of the α-cyano-4-fluoro3-phenoxybenzyl meta-halo pyrethrate as an insecticide.

In particular, the present invention provide a use of the compound of formula (I), stereoisomers thereof or the mixture of these stereoisomers in the preparation of an insecticide for controlling or killing vectors in the public hygiene and disease control and insects, nematodes, and acarids parasitizing agricultural animals and plants.

The present invention also relates to a method for controlling mosquitoes, cockroaches or houseflies, comprising applying, the compound of formula (I), stereoisomers thereof or the mixture of these stereoisomers.

In the fifth aspect of the present application, it is provided a pesticide composition comprising the compound of formula (I), stereoisomers thereof or the mixture of these stereoisomers, and an agriculturally acceptably inert carrier. If desired, one or more other insecticides can be added to the α-cyano-4-fluoro3-phenoxy benzyl meta-halo pyrethrate (I); or a surfactant and/or a solvent may be added to guarantee the active ingredients uniformly distributed. The composition is preferably in the form of a powder, a granule, or an emulsion.

MODES FOR CARRYING OUT THE INVENTION

The invention is further illustrated in conjunction with the following examples. It is appreciated that the present invention is not limited by these examples.

Preparation Method 1

Scheme 1

1.1. The preparation of (1R)-trans 3-(2-chlorovinyl)-2,2-dimethylcyclopropane carboxylate (meta-chloro pyrethric acid)

1.1.1 The Preparation of Methyl Primary Pyrethrate 10 g of (1R)-trans-primary pyrethric acid and 15 mL of thionyl chloride were added to a 100 mL one necked flask and was stirred for 5 hours in an oil bath of 35° C. The excessive thionyl chloride was removed by water pump under reduced pressure and the residue was diluted with 20 mL of anhydrous benzene.

11 g of anhydrous methanol, 8 mL of pyridine, and 20 mL of benzene were added to a 100 mL three-necked flask, and cooled in an ice-water bath. To the resulting mixture, the above-prepared acyl chloride solution in benzene was added dropwise under nitrogen atmosphere, after which the ice-water bath was removed and the mixture was stirred overnight at room temperature. A lot of white solids precipitated out of the reaction liquid. The solids were removed by filtration the next day and the filtrate was washed with 5% aqueous NaOH solution, 5% hydrochloric acid solution and saturated sodium bicarbonate solution and saturated NaCl solution successively, and extracted with ethyl ether. The organic phase was dried over anhydrous magnesium sulpate and anhydrous sodium sulpate. After the rotary evaporation of ethyl ether, benzene and pyridine were removed by a water pump under reduce pressure and the residue was distilled under reduced pressure by an oil pump to provide a fraction of 70~75° C./100 Pa (colorless liquid) 8.6 g, yield 79.6%.

1.1.2 The Preparation of (1R)-trans-methyl caronaldehydate 8 g of the methyl primary pyrethrate, 50 mL of glacial acetic acid were added to a 100 mL three necked flask and cooled by an ice-water bath to 12~15° C. A gas mixture of $O_3/O_2$ was introduced and the reaction was followed by TLC until the point of the starting materials disappeared. $N_2$ was introduced for 2 hours to evict the residual $O_3$ in the system. The temperature was controlled below 15° C. and 14 g of activated zinc powder was added in several portions. After addition, the mixture was further stirred for 2 hours, after which the zinc dregs were removed and water was added to the mixture. The resulting mixture was extracted with dichloromethane and dried over anhydrous magnesium sulpate. The solvent was removed by rotary evaporation and the residue was distilled under reduced pressure by an oil pump under nitrogen atmosphere and the fraction of 70-80° C./100 Pa (a colorless liquid) was collected, 4.5 g, yield 65%.

1.1.3 The Preparation of methyl 2,2-dimethyl-3-(2-chlorovinyl)cyclopropane carboxylate (methyl meta-chloro pyrethrate)

2.51 g of $Ph_3P^+CH_2Cl.Br^-$ was added to a 100 mL round-bottomed flask, evacuated and filled with nitrogen, and then 20 mL of anhydrous THF was added and the mixture was cooled by liquid nitrogen. The mixture was added with 0.85 g of $KOC(CH_3)_3$ solution in THF (the reaction liquid turned red) and reacted at low temperature for 1.5 hours. 1 g (1R)-trans-methyl caronaldehydate solution in THF (8 ml) was added and the liquid nitrogen was removed after 20 minutes and the mixture was reacted at room temperature for 6 hours. The reaction liquid was poured into 40 mL of ice-water and extracted with ethyl ether. The organic phase was dried over anhydrous magnesium sulpate. The solvent was removed by rotary evaporation and the crude product was purified by column chromatography (eluate: petroleum ether/ethyl acetate=200/1) to afford 0.7 g of colorless liquid, yield 58.3%. $^1$H NMR (CDCl$_3$) δ: 1.18 (s, 3H, cyclic-CH$_3$), 1.25 (s, 3H, cyclic-CH$_3$), 1.56~1.58 (t, 1H, J=6 Hz, cyclic-H), 2.04~2.05 (m, 1H, cyclic-H), 3.68, 3.69 (2s, 3H, COOCH$_3$), 5.47~5.51 (t, 0.39×1H, J=8 Hz, Z-=CH), 5.65~5.70 (dd, 0.61×1H, $J_1=J_2$=14 Hz, E-=CH), 6.06 (d, 0.61×1H, J=14 Hz, E-=CHCl), 6.14 (d, 0.39×1H, J=8 Hz, Z-=CHCl).

1.1.4 The preparation of (1R)-trans-2,2-dimethyl-3-(2-chlorovinyl)cyclopropane carboxylic acid (meta-chloro pyrethric acid)

To a 100 ml one necked flask, 0.5 g of NaOH, 1.5 ml of water, 15 ml of methanol, 1.6 g of methyl meta-chloro pyrethrate and 0.4 g of tetrabutylammonium bromide were successively added. The resulting mixture was heated under refluxing. The heating was not stopped until the point of the starting material disappeared. Methanol was removed by rotary evaporation and the residue was diluted with water, adjusted to a pH of 2-3 by adding in dropwise 10% hydrochloric acid, extracted with ethyl acetate and dried over anhydrous magnesium sulfate. The solvent was removed to give 1.3 g of liquid, yield 83%, wherein the ratio of the Z- to E-isomer was 0.39:0.61. IR (KBr): 2966, 1690, 1220, 935 cm$^{-1}$. $^1$H NMR (CDCl$_3$) δ: 1.19 (3H, cyclic-CH$_3$), 1.28 (s, 0.61×3H, cyclic-CH$_3$), 1.34 (s, 0.39×3H, cyclic-CH$_3$), 1.58~1.60 (t, 1H, J=5 Hz, cyclic-H), 2.07~2.10 (dd, 0.61×1H, $J_1=J_2$=5 Hz, cyclic-H), 2.43~2.46 (dd, 0.39×1H, $J_1=J_2$=5 Hz, cyclic-H), 5.48~5.51 (t, 0.39×1H, J=8 Hz, Z-=CH), 5.66~5.70 (dd, 0.61×1H, $J_1=J_2$=13 Hz, E-=CH), 6.09 (d, 0.61×1H, J=13 Hz, E-=CHCl), 11.5 (b, 1H, COOH). $[α]_D$=+28 (ethanol)

1.2 The preparation of cis-3-(E-2-chlorovinyl)-2,2-dimethylcyclopropane carboxylic acid Meta-chloro pyrethric acid was obtained by using the cis-primary pyrethric acid as a staring material according to the procedures used in Method 1.1 and then recrystallized by ethyl acetate to afford colorless cis-3-(E-2-chlorovinyl)-2,2-dimethylcyclopropane carboxylic acid crystal. Melting point: 103-105° C. $^1$H NMR (CDCl$_3$) δ: 1.20, 1.27 (2s, 6H, cyclic-CH$_3$); 1.74 (d, 1H, J=8 Hz, cyclic-CH); 1.89~1.92 (m, 1H, cyclic-CH); 6.08 (d, 1H, J=13 Hz, (E)-HClC=); 6.22 (dd, 1H, $J_{1=8}$ Hz, $J_2$=13 Hz, (E)=CH—); 11.97 (s, 1H, —COOH), IR (film) v: 2964, 1692, 1225, 937 cm$^{-1}$.

1.3 The preparation of trans-3-(2-chlorovinyl)-2,2-dimethylcyclopropane carboxylic acid Trans-meta-chloro pyrethric acid was obtained by using the racemic trans-primary pyrethric acid as a staring material according to the procedures used in Method 1.1, which was yellow and viscous, wherein the ratio of the Z- to the E-isomer was 33:67. $^1$H NMR (CDCl13) δ: 1.21 (s, 3H, cyclic-CH3); 1.28 (s, 3H, cyclic-CH3); 1.60~1.62 (m, 0.67×1H, cyclic-CH); 1.74 (d, 0.33×1H, J=5 Hz, cyclic-CH); 2.07~2.10 (m, 0.67×1H, cyclic-CH); 2.44~2.46 (m, 0.33×1H, cyclic-CH); 5.46 (t, 0.33×1H, $J_1=J_2$=7 Hz, (Z)=CH—); 5.66~5.08 (dd, 0.67×1H, $J_1=J_2$=13 Hz, (E)=CH—); 6.08~6.11 (d, 0.67×1H, J=13 Hz, (E)-HClC=); 6.15~6.16 (d, 0.33×1H, J=7 Hz, (Z)HClC=); 11.68 (s, 1H, —COOH); IR (film) v: 2966, 1690, 1220, 935 cm$^{-1}$.

1.4 The preparation of 3-(2-chlorovinyl)-2,2-dimethylcyclopropane carboxylic acid (meta-chloro pyrethric acid)

A saffron yellow and viscous product was obtained by using a primary pyrethric acid having a ratio of cis to trans isomer of 8:2 as a staring material according to the procedures used in Method 1.1, wherein; E/Z=5:1. $^1$H NMR (CDCl$_3$) δ: 1.20~1.30 (m, 6H, cyclic-CH3); 1.60~1.74 (m, 0.2×1H, cyclic-CH); 1.89~1.92 (m, 0.8×1H, cyclic-CH); 2.07~2.34 (m, 0.2×1H, cyclic-CH); 5.46~5.08 (m, 0.2×1H, =CH—); 6.08~6.22 (m, 0.8×1H, =CH—); 11.47 (s, 1H, —COOH); IR (film) v: 2965, 1691, 1224, 936 cm$^{-1}$.

Preparation Method 2

Scheme 2

2.1. The preparation of (1R)-trans-3-(2-bromovinyl)-2,2-dimethylcyclopropane carboxylic acid (meta-bromo pyrethric acid)

2.1.1 The preparation of methyl 2,2-dimethyl-3-(2-bromovinyl)cyclopropane carboxylate (methyl meta-bromo pyrethrate)

9.3 g of bromomethyltriphenylphosphonium bromide was added to a 250 mL of round-bottomed flask, evacuated, filled with nitrogen and 40 ml of anhydrous ethyl ether, 2.1 ml of piperidine were added. The mixture was stirred and cooled to −70~60° C. by liquid nitrogen. 9.5 ml of 2.2 mol/L of butyl lithium was added and stirred at low temperature for 1.5 hours and then the solution of 3.3 g of methyl caronaldehydate in 10 ml of benzene was added and stirred at low temperature for 20 minutes. Then the mixture was reacted at room temperature for 3 days (a lot of light yellow solids precipitated out of the reaction flask and the reaction liquid is milk white). The mixture was filtrated by sucking, and the solid was washed with anhydrous ethyl ether. The filtrate was washed with 10% of sulfuric acid and saturated NaCl successively and dried over anhydrous magnesium sulplate. The solvent was removed by rotary evaporation, and the crude product was purified by column chromatography to afford 1.9 g of colorless liquid, yield 39%.

2.1.2 The preparation of (1R)-trans-2,2-dimethyl-3-(2-bromovinyl)cyclopropane carboxylic acid (meta-bromo pyrethric acid)

0.5 g of NaOH, 1.5 ml of water, 15 ml of methanol, 1.9 g of methyl meta-bromo pyrethrate and 0.4 g of tetrabutyl ammonium bromide were added to a 100 mL one necked flask, and heated under refluxing. The heating was not stopped until the points of the starting materials disappeared. Methanol was removed by rotary evaporation and the residue was diluted with water and adjusted to a pH of 2~3 by adding dropwise 10% hydrochloric acid and extracted with ethyl acetate and the filtrate was dried over anhydrous magnesium sulplate. The solvent was removed by rotary evaporation to afford 1.4 g of liquid, yield 83%. The ratio of the Z- to the E-isomer was 0.64:0.36. IR (KBr): 1703, 1215, 938 cm$^{-1}$. $^1$H NMR (CDCl$_3$) δ: 1.21 (s, 0.64×3H, cyclic-CH$_3$), 1.26 (s, 0.36×3H, cyclic-CH$_3$), 1.29 (s, 0.64×3H, cyclic-CH$_3$), 1.36 (s, 0.36× 3H, cyclic-CH$_3$), 1.62~1.63 (d, 0.64×1H, J=4 Hz, cyclic-H), 1.98 (d, 0.36×1H, J=4 Hz, cyclic-H), 2.08~2.10 (m, 0.64×1H, cyclic-H), 2.38~2.41 (m, 0.36×1H, cyclic-H), 5.86~5.89 (t, 0.36×1H, J=7 Hz, Z-=CH), 5.92~5.97 (m, 0.64×1H, E-=CH), 6.19 (d, 0.64×1H, J=14 Hz, E-=CHBr), 6.31 (d, 0.36×1H, J=7 Hz, 10.5 (b, 1H, COOH). [α]$_D$=+26 (ethanol).

2.2 The Preparation of the Cis-Meta-Bromo Pyrethric Acid

A jacinth and viscous meta-bromo pyrethric acid was obtained by using the cis-primary pyrethric acid as a staring material according to the procedures used in Method 2.1, wherein the ratio of the Z- to the E-isomer was 0.4:0.6. $^1$H NMR (CDCl$_3$) δ:1.22 (s, 0.4×6H, cyclic-CH$_3$); 1.29, 1.31 (2s, 0.62×6H, cyclic-CH$_3$); 1.75 (d, 0.6×1H, J=8 Hz, (Z) cyclic-CH); 1.85 (d, 0.4×1H, J=9 Hz, (E)cyclic-CH); 1.91 (t, 0.6× 1H, J$_1$=J$_2$=9 Hz, (E)cyclic-CH); 2.23~2.28 (m, 0.4×1H, (Z) cyclic-CH); 6.17 (d, 0.6×1H, J=13 Hz, (E)BrCH=); 6.30 (d, 0.4×1H, J=7 Hz, (Z)BrCH=); 6.45 (dd, 0.4×1H, J$_1$=J$_1$=7 Hz, (Z)=CH); 6.49 (dd, 0.6×1H, J$_1$=J$_2$=13 Hz, (E)=CH); 11.59 (s, 1H, —COOH); IR (film) v: 1703, 1215, 938 cm$^{-1}$.

Preparation Method 3

The preparation of cis-3-(E-2-fluorovinyl)-2,2-dimethylcyclopropane carboxylic acid (meta-fluoro pyrethric acid)

11.5 mmol of cis-difluoropyrethric acid was placed in a 25 ml of one-necked flask, to which 5 ml of thionyl chloride was added, and the mixture was reacted at 40-50° C. for 4 hours. The excessive thionyl chloride was removed under reduced pressure and 10 ml of anhydrous benzene was added. The solvent was removed completely again and 5 ml of anhydrous dichloromethane was added; 23 mmol of 2-methyl-2-amino propanol and 20 ml of anhydrous dichloromethane were added to a 50 ml three-necked flask, and then the above-prepared acyl chloride solution in dichloromethane was added slowly and dropwise. The resulting mixture was stirred at room temperature for 2 hour. The solvent was removed under reduced pressure and 10 ml of anhydrous benzene was added to the mixture and stirred. 5 ml of thinly chloride was added dropwise and the mixture was reacted at room temperature for 2 hours. The solvent was removed again and the residue was cooled in an ice-water bath. To the residue was added 10% NaOH to basic. The mixture was stirred at room temperature for 0.5 hour and extracted with ethyl ether. The organic phase was dried and the solvent was removed. 20 ml of toluene and 5 ml of Vitride (70% solution in toluene) were added and refluxed for 4 hours. Then the mixture was cooled to room temperature. 10 ml of water and 5% NaOH were added slowly. The mixture was refluxed for 1 hour and washed with saturated NaCl solution. The organic phase was dried and the solvent was removed. The crude product was purified by column chromatography (petroleum ether: ethyl acetate=10:1) and the E-product obtained by column chromatography was dissolved in 20 ml of 3N hydrochloric acid solution, and refluxed for 1 hour, and extracted with ethyl ether (20 ml×3). The organic phase was washed with water and dried over anhydrous Na$_2$SO$_4$. The solvent was removed to afford E-cis-meta-fluoro pyrethric acid, total yield 50%. $^1$H NMR (CDCl$_3$) δ:1.17 (3H, cyclic-CH$_3$), 1.28 (s, 3H, cyclic-CH$_3$), 1.45 (d, 1H, J=5 Hz, cyclic-H), 1.97 (dd, 1H, J$_1$=6 Hz, J$_2$=9 Hz, cyclic-H), 5.10~5.28 (m, =CH), 6.66 (dd, 1H, J$_1$=84 Hz, J$_2$=11 Hz, E-=CHF), 11.5 (b, 1H, COOH).

Preparation Example 1

The preparation of cis/trans-α-cyano-3-phenoxy-4-fluoro-benzyl-2,2-dimethyl-3-(E/Z-2-chlorovinyl) cyclopropane carboxylate 5.7 mmol of mixed-meta-chloro pyrethric acid obtained by the preparation method 1.4 and 5.0 ml of thionyl chloride were stirred for 4-5 hours, after which, the excessive thionyl chloride was removed by a water pump under reduced pressure and the residue was diluted with 5.0 mL of benzene for use.

5.7 mmol of 4-fluoro-3-phenoxybenzaldehyde, 30 ml of cyclohexane, 0.45 ml of pyridine and 1 g of KCN were added to a 100 mL of three-necked flask to form a saturated aqueous solution, which was stirred at room temperature for 20 minutes. The above-prepared acyl chloride was added slowly and dropwise to the mixture and stirred at room temperature overnight and then 20 ml of water was added. The layers were separated and the organic layer was washed with 10 mL of 5% NaOH solution, 5% of hydrochloric acid and saturated NaCl solution successively and dried. The solvent was removed to obtain a light yellow and viscous crude product, which was purified by column chromatography (petroleum ether/ethyl acetate=10/1) to afford a light yellow liquid, yield 82%. $^1$H NMR (CDCl$_3$) δ: 1.1649~1.29 (m, 6H, cyclic-CH$_3$); 1.61~1.77 (m, 1H, cyclic-CH); 1.89~2.15 (m, 1H, cyclic-CH); 6.06 (m, 1H, ClHC=); 5.64~5.70 (m, 0.2×1H, =CH); 6.12~6.20 (m, 0.8×1H, =CH); 6.27~6.33 (m, 1H, CH—CN); 6.98~7.02 (m, 2H, ArH); 7.11~7.39 (m, 6H, ArH).

Preparation Example 2

The preparation of cis-α-cyano-3-phenoxy-4-fluoro-benzyl-2,2-dimethyl-3-(2-chlorovinyl)cyclopropane carboxylate The target compound was obtained by esterification according to the method used in Example 1 using the cis-meta-chloro pyrethric acid obtained by the preparation method 1.2. $^1$H NMR (CDCl$_3$) δ: 1.16, 1.18, 1.21, 1.28 (4s, 6H, cyclic-CH$_3$); 1.77 (dd, 1H, J$_1$=J$_2$=8 Hz, cyclic-CH); 1.89~1.90 (m, 1H, cyclic-CH); 6.06 (m, 1H, ClHC=);

6.14~6.20 (m, 1H, =CH); 6.27 (2s, 1H, CH—CN); 6.98~6.99 (m, 2H, ArH); 7.11~7.14 (m, 1H, ArH); 7.19~7.27 ((m, 3H, ArH); 7.32~7.35 (m, 2H, ArH).

Preparation Example 3

The preparation of Trans-α-cyano-3-phenoxy-4-fluoro-benzyl-2,2-dimethyl-3-(2-chlorovinyl)cyclopropane carboxylate 5.7 mmol of trans-meta-chloro pyrethric acid obtained by the preparation method 1.3 and 5.0 ml of thionyl chloride were stirred in an oil bath of 50° C. for 4-5 hours, after which, the excessive thionyl chloride was removed by a water pump under reduced pressure and the residue was diluted with 5.0 mL of benzene for use.

5.7 mmol of α-cyano-4-fluoro-3-phenoxy benzyl alcohol, 30 ml of cyclohexane, 0.45 ml of pyridine were added to a 100 mL three-necked flask and stirred at room temperature.

To the mixture, the above-prepared acyl chloride was slowly added. After 20 minutes, the addition was complete. The mixture was stirred overnight at room temperature and then 20 ml of water was added. The layers were separated and the organic phase was washed successively with 10 mL of 5% NaOH solution, 5% of hydrochloric acid solution and saturated brine, and dried. The solvent was removed to afford a light yellow and viscous product. The crude product was purified by column chromatography (petroleum ether/ethyl acctate=10/1) to afford a light yellow liquid, yield 80.0%. NMR (CDCl$_3$) δ: 1.18, 1.19, 1.22, 1.29 (4s, 6H, cyclic-CH$_3$); 1.61~1.64 (m, 1H, cyclic-CH); 2.12~2.15 (m, 1H, cyclic-CH); 5.64~5.70 (m, 1H, =CH); 6.12 (m, 1H, ClHC=); 6.31 (s, 0.36×1H, CH—CN); 6.33 (s, 0.64×1H, CH—CN); 7.01~7.02 (m, 2H, ArH); 7.15~7.20 (m, 2H, ArH); 7.25~7.30 (m, 2H, ArH); 7.36~7.39 (m, 2H, ArH).

Preparation Example 4

The preparation of (1R)-Trans-α-cyano-3-phenoxy-4-fluoro-benzyl-2,2-dimethyl-3-(2-bromovinyl)cyclopropane carboxylate The target compound was obtained by esterification according to the method used in Example 1 using the (1R)-trans-meta-bromo pyrethric acid obtained by the preparation method 2.1. $^1$H NMR (CDCl$_3$) δ: 1.23, 1.25, 1.27, 1.35 (4s, 6H, cyclic-CH$_3$), 1.62~1.63 (d, 0.64×1H, J=4 Hz, cyclic-H), 1.98 (d, 0.36×1H, J=4 Hz, cyclic-H), 2.08~2.10 (m, 0.64×1H, cyclic-H), 2.38~2.41 (m, 0.36×1H, cyclic-H), 5.86~5.89 (t, 0.36×1H, J=7 Hz, Z—CH), 5.92~5.97 (dd, 0.64×1H, J$_1$=J$_2$=14 Hz, E-=CH), 6.19 (d, 0.64×1H, J=14 Hz, E-=CHBr), 6.31 (d, 0.36×1H, J=7 Hz, Z-=CHBr), 7.01~7.02 (m, 2H, ArH); 7.15~7.20 (m, 2H, ArH); 7.25~7.30 (m, 2H, ArH); 7.36~7.39 (m, 2H, ArH); [α]$_D$=−7 (ethanol).

Preparation Example 5

The preparation of cis-α-cyano-3-phenoxy-4-fluoro-benzyl-2,2-dimethyl-3-(E-2-fluorovinyl)cyclopropane carboxylate The target compound was obtained by esterification according to the method used in Example 3 using the cis-2E-meta-fluoro pyrethric acid obtained by the preparation method 3. $^1$H NMR (CDCl$_3$) δ: 1.17 (3H, cyclic-CH$_3$), 1.28 (s, 3H, cyclic-CH$_3$), 1.45 (d, 1H, J=5 Hz, cyclic-H), 1.97 (dd, 1H, J$_1$=6 Hz, J$_2$=9 Hz, cyclic-H), 5.10~5.28 (m, =CH), 6.66 (dd, 1H, J$_1$=84 Hz, J$_2$=11 Hz, E-=CHF), 7.03~7.05 (m, 2H, ArH); 7.15~7.20 (m, 2H, ArH); 7.24~7.31 (m, 2H, ArH); 7.34~7.37 (m, 2H, ArH).

Comparative Example 1

The preparation of cis-2,3,5,6-tetrafluoro-4-benzyl-3-(E-2-chlorovinyl)-2,2-dimethylcyclopropane carboxylate The target compound was obtained by esterification according to the method used in Example 2 using the cis-meta-chloro pyrethric acid and tetrafluorobenzyl alcohol obtained by the preparation method 1.2. $^1$H NMR (CDCl$_3$) δ(ppm): 1.21 (s, 3H, cyclic-CH$_3$); 1.29 (s, 3H, cyclic-CH$_3$); 1.77 (d, 1H, J=9 Hz, cyclic-CH); 1.87 (t, 1H, J=9 Hz, cyclic-CH); 5.09~5.15 (m, 2H, COOCH$_2$); 6.06 (d, 1H, J=13 Hz, (E)-HCl=); 6.21 (dd, 1H, J$_1$=9 Hz, J$_2$=13 Hz, (E)HCl=); 7.02~7.07 (m, 1H, ArH).

Comparative Example 2

The preparation of cis-2,3,5,6-tetrafluoro-4-methyl benzyl-3-(E-2-chlorovinyl)-2,2-dimethylcyclopropane carboxylate The target compound was obtained by esterification according to the method used in Example 2 using the cis-meta-chloro pyrethric acid and p-methyl tetrafluorobenzyl alcohol obtained by the preparation method 1.2. $^1$H NMR (CDCl$_3$) δ(ppm): 1.19 (s, 3H, cyclic-CH$_3$); 1.28 (s, 3H, cyclic-CH$_3$); 1.70 (d, 1H, J=9 Hz, cyclic-CH); 1.83 (t, 1H, J=9 Hz, cyclic-CH); 2.28~2.29 (m, 3H, ArCH$_3$); 5.15 (m, 2H, COOCH$_2$); 6.05 (d, 1H, J=13 Hz, (E)HClC=); 6.21 (dd, 1H, J$_1$=9 Hz, J$_2$=13 Hz, (E)HClC=).

Comparative Example 3

The preparation of cis-pentafluorobenzyl-3-(E-2-chlorovinyl)-2,2-dimethyl cyclopropane carboxylate The target compound was obtained by esterification according to the method used in Example 2 using the cis-meta-chloro pyrethric acid and pentafluorobenzyl alcohol obtained by the preparation method 1.2. $^1$H NMR (CDCl$_3$) δ(ppm): 1.19 (s, 3H, cyclic-CH$_3$); 1.28 (s, 3H, cyclic-CH$_3$); 1.71 (d, 1H, J=8 Hz, cyclic-CH); 1.84 (t, 1H, J=8 Hz, cyclic-CH); 5.15~5.25 (m, 2H, COOCH$_2$); 6.06 (d, 1H, J=14 Hz, (E)-HCl=); 6.23 (m, 1H, (E)-HCl=).

Comparative Example 4

The preparation of trans-2,3,5,6-tetrafluoro-4-benzyl-3-(2-chlorovinyl)-2,2-dimethylcyclopropane carboxylat The target compound was obtained by esterification according to the method used in Example 2 using the trans-meta-chloro pyrethric acid and 2,3,5,6-tetrafluorobenzyl alcohol obtained by the preparation method 1.3. $^1$H NMR (CDCl$_3$) δ(ppm): 1.17 (s, 3H, cyclic-CH$_3$); 1.25 (s, 3H, cyclic-CH$_3$); 1.61 (d, 1H, J=5 Hz, cyclic-CH); 2.07~2.09 (m, 0.7×1H, cyclic-CH); 2.41~2.43 (m, 0.3×1H, cyclic-CH); 5.13~5.15 (m, 2H, —COOCH$_2$); 5.49 (t, 0.3×1H, J=8 Hz, (Z)=CH—); 5.65 (dd, 0.7×1H, J$_1$=J$_2$=14 Hz, (E)=CH—);

6.08 (d, 0.7×1H, J=14 Hz, (E)HCl═); 6.16 (d, 0.3×1H, J=8 Hz, (Z)HCl═); 7.02~7.07 (m, 1H, ArH).

Comparative Example 5

The preparation of trans-2,3,5,6-tetrafluoro-4-methylbenzyl-3-(2-chlorovinyl)-2,2-dimethylcyclopropane carboxylate The target compound was obtained by esterification according to the method used in Example 2 using the trans-meta-chloro pyrethric acid and 2,3,5,6-tetrafluoro-4-methylbenzyl alcohol obtained by the preparation method 1.3. $^1$H NMR (CDCl$_3$) δ (ppm): 1.16 (s, 3H, cyclic-CH$_3$); 1.24 (s, 3H, cyclic-CH$_3$); 1.55 (d, 1H, J=6 Hz, cyclic-CH); 2.0~52.08 (m, 0.7×1H, cyclic-CH); 2.29 (s, 3H, ArCH$_3$) 2.4~2.43 (m, 0.3×1H, cyclic-CH); 5.16-5.19 (m, 2H, —COOCH$_2$); 5.47 (t, 0.3×1H, J=8 Hz, (Z)═CH—); 5.66 (dd, 0.7×1H, J$_1$=J$_2$=13 Hz, (E)═CH—) 6.06 (d, 0.7×1H, J=13 Hz, (E)HCl═); 6.14 (d, 0.3×1H, J=8 Hz, (Z)HCl═).

Comparative Example 6

The preparation of trans-pentafluorobenzyl-3-(2-chlorovinyl)-2,2-dimethyl cyclopropane carboxylate The target compound was obtained by esterification according to the method used in Example 2 using the trans-meta-chloro pyrethric acid and pentatluorobenzyl alcohol obtained by the preparation method 1.3. $^1$H NMR (CDCl$_3$) δ (ppm): 1.17 (s, 3H, cyclic-CH$_3$); 1.25 (s, 3H, cyclic-CH$_3$); 1.57 (d, 1H, J=5 Hz, cyclic-CH); 2.06~2.09 (m, 0.7×1H, cyclic-CH); 2.41~2.43 (m, 0.3×1H, cyclic-CH); 5.17~5.19 (m, 2H, —COOCH$_2$); 5.48 (t, 0.3×1H, J=7 Hz, (Z)═CH—) 5.64 (dd, 0.7×1H, J$_1$=J$_2$=13 Hz, (E)═CH—); 6.07 (d, 0.7×1H, J=13 Hz, (E)HCl═); 6.15 (d, 0.3×1H, J=8 Hz, (Z)HCl═).

Comparative Example 7

The preparation of cis-α-cyano-3-phenoxybenzyl-2,2-dimethyl-3-(2-bromovinyl)cyclopropane carboxylate The target compound was obtained by esterification according to the method used in Example 1 using the cis-meta-bromo pyrethric acid and 3-phenoxy benzaldehyde obtained by the preparation method 2.2. $^1$H NMR (CDCl$_3$) δ: 1.12~1.25 (m, 2×3H, cyclic-CH$_3$); 1.74 (d, 0.6×1H, J=8 Hz, cyclic-CH); 1.82~1.91 (m, 1H, cyclic-CH); 2.24 (m, 0.4×1H, cyclic-CH); 6.09 (d, 0.6×1H, J=13 Hz, (E)-BrCH═); 6.14 (d, 0.4×1H, J=8 Hz (Z)—BrCH═); 6.26 (s, 0.6×1H, CNCH); 6.32 (s, 0.4×1H, CNCH); 6.36~6.99 (m, 1H, ═CH); 6.95~6.99 (m, 3H, ArH); 7.07~7.10 (m, 2H, ArH); 7.15~7.18 (m, 1H, ArH); 7.28~7.34 (m, 3H, ArH).

Comparative Example 8

The preparation of trans-α-cyano-3-phenoxybenzyl-2,2-dimethyl-3-(2-chlorovinyl)cyclopropane carboxylate The target compound was obtained by esterification according to the method used in Example 1 using the trans-meta-chloro pyrethric acid and 3-phenoxy benzaldehyde obtained by the preparation method 1.3. $^1$NMR (CDCl$_3$) δ: 1.20, 1.23, 1.24, 1.32 (4s, 6H, cyclic-CH$_3$); 1.66~1.68 (m, 1H, cyclic-CH); 2.12~2.17 (m, 1H, cyclic-CH); 5.66~5.72 (m, 1H, ═CH); 6.09~6.22 (m, 1H, ClHC); 6.36~6.42 (m, 1H, CH—CN); 7.047~7.096 (m, 3H, ArH); 7.153~7.201 (m, 2H, ArH); 7.261~7.277 ((m, 1.1H, ArH); 7.380~7.438 (m, 3H, ArH).

Biological Assays

Example 1

The Killing Effect on Wiggler

The following pyrethrates were tested as representatives according to the method recommended by the World Health Organization (WHO) (Zongbing ZHANG, the assay of toxicity of insecticides, the Science Press, 1988), the commonly used testing breed, *Culex pipiens pallens* fourth instar wiggler is used as a subject for biological assay, test temperature: 26±1° C., humidity: 70±10%; immersing method: a solution of a certain amount the compound to be tested in acetone was mixed evenly with pure water in the gradually decreasing concentration of 500, 250, 100, 50, 25, 12.5, 6.25, 3.125, 1, 0.5, 0.25, 0.1, 0.05, 0.025, 0.01, 0.005, 0.0025, 0.0001 mg/L, and the mortality of wiggler after 24 hours was calculated and LC$_{50}$ was calculated to preliminarily evaluate the insecticidal activity. The results were shown in Table I. Compound 1-5 are representative examples of the compound of formula (I) of the present invention: the compounds involved in preparation Example 1-5 were prepared;

Compound 6~11 are representative examples of polyfluorobenzyl meta-halo pyrethrate mentioned in CN1044650A, corresponding to the compounds of Comparative Example 1-6 of the present specification respectively;

Compound 12~13 are representative examples of α-cyano-3-phenoxy benzyl dihalo-pyrethrate mentioned by Elliott in Pestic. Sci. 17, 1986, 708, corresponding to the compounds of Comparative Example 7 and 8 of the present specification respectively;

(*Note: the Compound No. in the following examples is designated according to the same principle as above)

At the same time, their relative toxicities were compared with those of Cypermethrin, and Deltamethrin.

TABLE 1

The killing effect of the compound of formula (I) of the present invention on wiggler

| Compound No. | LC$_{50}$ (mg/L)(95% confidence interval) | Relative toxicity |
|---|---|---|
| 1 | 0.00055 (0.00045~0.00067) | 1927 |
| 2 | 0.00047 (0.00042~0.00054) | 2255 |
| 3 | 0.0055 (0.0042~0.0072) | 193 |
| 4 | 0.0027 (0.0012~0.0045) | 393 |
| 5 | 0.00061 (0.00049~0.00078) | 1740 |
| 6 | 0.4810 (0.4621~0.5006) | 2 |
| 7 | 0.0741 (0.0699~0.0786) | 14 |
| 8 | 0.0801 (0.0756~0.0850) | 13 |
| 9 | 0.2492 (0.2394~0.2594) | 4 |
| 10 | 0.0578 (0.0553~0.0603) | 18 |

TABLE 1-continued

The killing effect of the compound of formula (I) of the present invention on wiggler

| Compound No. | LC$_{50}$ (mg/L)(95% confidence interval) | Relative toxicity |
|---|---|---|
| 11 | 0.2041 (0.1991~0.2093) | 5 |
| 12 | 0.0108 (0.0101~0.0116) | 98 |
| 13 | 0.0527 (0.0484~0.0574) | 20 |
| Deltamethrin | 0.0012 (0.0008~0.0018) | 883 |
| Cypermethrin | 0.0106 (0.0094~0.0119) | 100 |

Example 2

The Effect on *Mythimna separata*

The killing effect on *Mythimna separata* was tested using Compounds 2 and 3, which are representative examples of the compound of formula (I) of the present invention, Compound 9, polyfluorobenzyl meta-halo pyrethrate, which has the highest insecticidal activity to *Mythimna separata* as a control example.

*Mythimna separata*: test temperature: 26±1° C., humidity: 70±10%; the corn leaves was immersed, and then were taken out after they were dipped in a liquor in dimethyl sulfoxide for 5 seconds. The liquor was dried in the shade and the corn leaves were cut away to feed larvae at the beginning of the third instar. Each treatment was done in triplicate. The number of killed insects was counted after 48 hours to calculate the mortality. The test result was shown in Table 2.

TABLE 2

The killing effect of the compounds of formula (I) of the present invention on *Mythimna separata*

| Test concentration ppm | The average mortality of Compound 9 the number of the killed insects/the number of the total tested insects | The average mortality of Compound 3 the number of the killed insects/the number of the total tested insects | The average mortality of Compound 2 the number of the killed insects/the number of the total tested insects |
|---|---|---|---|
| 500 | 100% 10/10, 10/10, 10/10 | 100% 10/10, 10/10, 10/10, | 100% 10/10, 10/10, 10/10, |
| 50 | 100% 10/10, 10/10, 10/10, | 100% 10/10, 10/10, 10/10, | 100% 10/10, 10/10, 10/10, |
| 5 | 0% 0/10, 0/10, 0/10, | 100% 10/10, 10/10, 10/10, | 100% 10/10, 10/10, 10/10, |
| 1 | 0% 0/10, 0/10, 0/10, | 0% 0/10, 0/10, 0/10, | 66.7% 6/10, 7/10, 7/10, |
| 0.5 | 0% 0/10, 0/10, 0/10, | 0% 0/10, 0/10, 0/10, | 33.3% 4/10, 3/10, 3/10, |
| 0.25 | / | / | 0% 0/10, 0/10, 0/10 |

Example 3

The Effect on Aphids

The killing effect on aphids was tested using Compound 2 and 3, which are representative examples of the compound of formula (I) of the present invention, Compound 9 as a control example. *Aphis medicaginis kock*; test temperature: 26±1° C., humidity: 70±10%; test method: immersion; adult insects together with bean sprouts were immersed in a liquor in dimethyl sulfoxide for 5 seconds, after which the bean sprouts were heeled in a solid support. Each treatment was done in triplicate. The number of the killed insects was checked after 24 hours to calculate the mortality. The test results were shown in Table 3.

TABLE 3

The killing effect of the compounds of formula (I) of the present invention on aphids

| Test concentration ppm | The average mortality of Compound 9 the number of the killed insects/the number of the total tested insects | The average mortality of Compound 3 the number of the killed insects/the number of the total tested insects | The average mortality of Compound 2 the number of the killed insects/the number of the total tested insects |
|---|---|---|---|
| 500 | 100% 23/23, 28/28, 30/30, | 100% 10/10, 10/10, 10/10, | 100% 22/22, 27/27, 25/25, |

TABLE 3-continued

The killing effect of the compounds of formula (I) of the present invention on aphids

| Test concentration ppm | The average mortality of Compound 9 the number of the killed insects/the number of the total tested insects | The average mortality of Compound 3 the number of the killed insects/the number of the total tested insects | The average mortality of Compound 2 the number of the killed insects/the number of the total tested insects |
|---|---|---|---|
| 50 | 18.8% 4/24, 7/33, 5/27, | 100% 26/26, 31/31, 22/22, | 100% 26/26, 21/21, 23/23, |
| 5 | 0% 0/30, 0/28, 0/35, | 83.70% 28/31, 26/28, 29/29, | 89.5% 23/25, 25/28, 27/31, |
| 1 | 0% 0/31, 0/28, 0/35, | 66.3% 9/14, 23/35, 20/29, | 84.3% 25/30, 30/34, 26/32, |
| 0.5 | 0% 0/25, 0/32, 0/29, | 0% 2/21, 3/29, 3/31, | 28.8% 5/21, 8/24, 7/24, |
| 0.25 | / | / | 0% 0/27, 0/24, 0/22, |

Example 4

The Effect on *Tetrangychus cinnabarinus*

The killing effect on acarids was tested using Compound 2 and 3, which are representative examples of the compound of formula (I) of the present invention, Compound 9 as a control example. *Tetrangychus cinnabarinus*, test temperature: 26±1° C. humidity: 70±10%; test method: immersion; adult insects together with horsebean leaves were immersed in a liquor in dimethyl sulfoxide for 5 seconds, after which the leaves were inserted into a small bottle. Each treatment was done in triplicate. The number of the killed insects was checked after 24 hours to calculate the mortality. The test results were shown in Table 4.

TABLE 4

The killing effect of the compounds of formula (I) of the present invention on *Tetrangychus cinnabarinus*

| Test concentration mg/L | The average mortality of Compound 9 the number of the killed insects/the number of the total tested insects | The average mortality of Compound 3 the number of the killed insects/the number of the total tested insects | The average mortality of Compound 2 the number of the killed insects/the number of the total tested insects |
|---|---|---|---|
| 500 | 0% 0/23, 0/29, 0/25, | 100% 32/32, 26/26, 29/29, | 100% 27/27, 34/34, 23/23, |
| 50 | 0% 0/33, 0/29, 0/27, | 7.8% 2/23, 1/19, 2/21, | 91.1% 21/23, 26/28, 25/28, |
| 5 | 0% 0/21, 0/28, 0/32, | 0% 0/24, 0/19, 0/30, | 11.9% 2/21, 4/29, 3/24, |
| 1 | 0% 0/32, 0/28, 0/21, | 0% 0/27, 0/22, 0/29, | 0% 0/27, 0/22, 0/29, |

Example 5

The Striking Down Effect on *Musca domestica*

The striking down effect on *Musca domestica* was tested using Compounds 2 and 3, which are representative examples of the compound of formula (I) of the present invention, Compound 9 as a control example. *Musca domestica*, an in-house cultured sensitive strain, the adult insects in eclosion for 3-5 days were used, and the male and female insects are half and half. Test temperature: 26±1° C., humidity: 70±10%, test method: liquid film contact method. 1 ml of 0.1% liquor in acetone was evenly coated on a 500 ml conical flask to form a film. After the film was dry, 20~25 adult insects were put into the flask, and the striking down time and striking down number were observed, and each treatment was done in triplicate. The test results were shown in Table 5.

TABLE 5

The striking down effect of the compounds of formula (I) of the present invention on *Musca domestica*

| | Compound 9 | Compound 3 | Compound 2 |
|---|---|---|---|
| $KT_{50}$ (score) | 9.51 | 5.80 | 3.49 |
| 95% confidence interval | (8.40~10.52) | (4.81~6.92) | (3.01~4.02) |

Example 6

The Striking Down Effect on Cockroaches

The striking down effect on *Blattela germanica* was tested using Compound 2 and 3, which are representative examples of the compound of formula (I) of the present invention, Compound 9 as a control example. *Blattela germanica*, an in-house cultured sensitive strain, male adult insects were used. Test temperature: 22±1° C., test method: liquid film contact method. A liquor in acetone was evenly coated at the amount of 54 mg/m² on the inner wall of a wild mouth bottle to form a film. After the film was dry, 10 adult insects were put into each bottle, and the striking down time and striking down number were observed, and each treatment was done in triplicate. The test results were shown in Table 6.

TABLE 6

The striking down effect of the compounds of formula (I) of the present invention on *Blattella germanica*

|  | Compound 9 | Compound 3 | Compound 2 |
|---|---|---|---|
| $KT_{50}$ (score) 95% confidence interval | 12.0 (10.81~3.12) | 8.14 (7.55~8.70) | 5.12 (4.71~5.55) |

COMPOSITION EXAMPLE 1

The Preparation of a Water-Based Concentrate

A uniform mixture was prepared from the following components:

| The compound of Preparation Example 1 | 0.1 g |
|---|---|
| tetramethrin | 2.0 g |
| Tween 80 | 0.2 g |
| water | 97.7 g |

Composition Example 2

The Preparation of an Emulsible Concentrate

A uniform mixture was prepared from the following components:

| The compound of Preparation Example 1 | 2.0 g |
|---|---|
| Tween 80 | 20.0 g |
| xylene | 78.0 g |

Example 7

Stability Test 0.15 mmol of the compound of Preparation Example 2 (cis-α-cyano-3-phenoxy-4-fluoro-benzyl-2,2-dimethyl-3-(2-chlorovinyl)cyclopropane carboxylate) and 0.15 mmol of the corresponding dichloride compound (cis-α-cyano-3-phenoxy-4-fluoro-benzyl-2,2-dimethyl-3-(2,2-dichlorovinyl) cyclopropane carboxylate) were added to two vessels separately, to which 50 ml of cyclohexane were added separately. They were irradiated by a 500 W ultraviolet lamp for 30 min respectively. Then to each of the vessels were added 0.15 mmol of n-hexane as an internal standard for gas chromatography analysis. 30% of the former was degraded by light and 14% of the latter was degraded by light, which indicates that the former is comparable with the theoretical prediction, and its light stability was higher than that of the primacy pyrethrate and lower than that of dihalopyrethrate, i.e., it has a suitable stability. The photodegradation rate of the former is 1.9 times of that of the latter. That is to say, if the same amounts were used, the residue of the former in the environment is lower than that of the latter.

The present invention has the following positive effects:

1. The compound of formula (I) of the present invention has a high insecticidal activity and a broad insecticidal spectrum: the relative toxicity of the compound in Example 2 to common household pest *Culex pipiens pallen* larvae is much higher than that of tetrafluorobenzyl meta-halo pyrethrate (125-1128 times of that of the compounds in comparative examples 1-6); is 2.55 times of that of deltamethrin, which has the highest insecticidal activity presently; 22.55 times of that of cypermethrin; it showed a high insecticidal activity to *Mythimna separata* which have a large volume and to which most of the insecticides showed a relatively low insecticidal activity; the average mortality rate of *Mythimna separata* was 66.7% at the low concentration of 1 mg/L, better than the pesticides such as deltamethrin. Similarly, it also showed a high insecticidal activity on aphids, in particular, the average mortality rate of aphids was 84.3% at the low concentration of 1 mg/L; it also showed a good insecticidal activity on acarids, on which the most of the pyrethroid insecticides, represented by deltamethrin and cypermethrin have no effect. The average mortality rate of *Tetrangychus cinnabarinus* was 91.1% at the low concentration of 50 mg/L. In addition, it is noteworthy that deltamethrin was a single chiral isomer having the highest activity of the eight optical isomers, and the compound of Example 2 is a racemate of four chiral isomers. If it is the same single chiral isomer, its relative toxicity is estimated to be 4*2.55=10 times of that of deltamethrin.

2. The compound of formula (I) of the present application has a high safety factor. The acute toxicity $LD_{50}$ of the compound prepared in Preparation Example 2 on rats by oral administration was: 116.5 mg/kg (male rats); 158 mg/kg (female rats). $LD_{50}$ of deltamethrin is 70~140 mg/Kg, comparable to that of the compound of formula (I) of the present application. Therefore, the safety factor (i.e. toxicity ratio) of the compound of formula (I) of the present application is 2.55 times better than that of Deltamethrin.

3. The compound of formula (I) of the present application can be easily synthesized with low cost, and can be easily industrialized: no matter compared with much expensive polyfluorobenzyl alcohol for the preparation of tetrafluorobenzyl meta-halopyrethrate, or compared with Deltamethrin with the single chiral isomer, whose atomic productivity is low, the starting material for preparing the compound of formula (I) of the present invention, 3-phenoxy-4-fluoro-benzaldehyde (III) and the compound α-cyano-3-phenoxy-4-fluoro-benzyl alcohol (IV) as well as the intermediate of meta-chloro pyrethric acid, methyl 3,3-dimethyl-4-pentenoate or pyrethric acid are produced in large scale at home and abroad, and the meta-chloro pyrethric acid can be directly used in esterification reaction without optical resolution, resulting a product of high activity.

4. The light stability of the compound of formula (I) of the present invention is higher than that of the primary pyrethrate and lower than that of the dihalopyrethrate due to the presence of asymmetrical metapyrethric acid and fluoro-containing structure, i.e. it has an appropriate stability. In addition, it has the advantages of quick efficiency and lowering the resistance of insects.

The invention claimed is:

1. A compound of formula (I), stereoisomers thereof or the mixture of these stereoisomers:

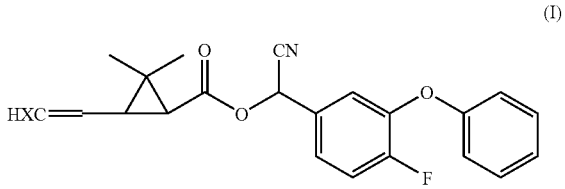

(I)

wherein: X represents F, Cl, or Br.

2. A compound, stereoisomers thereof or the mixture of these stereoisomers, wherein the compound is selected from the group consisting of:
α-cyano-3-phenoxy-4-fluoro-benzyl-2,2-dimethyl-3-(2-fluorovinyl)cyclopropane carboxylate,
α-cyano-3-phenoxy-4-fluoro-benzyl-2,2-dimethyl-3-(2-chlorovinyl)cyclopropane carboxylate, or
α-cyano-3-phenoxy-4-fluoro-benzyl-2,2-dimethyl-3-(2-bromovinyl)cyclopropane carboxylate.

3. The compound of claim 1, which is selected from:
cis/trans-α-cyano-3-phenoxy-4-fluoro-benzyl-2,2-dimethyl-3-(E/Z-2-chlorovinyl)cyclopropane carboxylate;
cis-α-cyano-3-phenoxy-4-fluoro-benzyl-2,2-dimethyl-3-(2-chlorovinyl)cyclopropane carboxylate;
trans-α-cyano-3-phenoxy-4-fluoro-benzyl-2,2-dimethyl-3-(2-chlorovinyl)cyclopropane carboxylate;
(1R)-trans-α-cyano-3-phenoxy4-fluoro-benzyl-2,2-dimethyl-3-(2-bromovinyl)cyclopropane carboxylate; or
cis-α-cyano-3-phenoxy-4-fluoro-benzyl-2,2-dimethyl-3-(E-2-fluorovinyl)cyclopropane carboxylate.

4. A process for the preparation of the compound of claim 1, comprising:
(a) condensing the compound of formula (V) with 3-phenoxy-4-fluoro-benzaldehyde of formula (III) in the presence of an alkali metal cyanide by esterification reaction; or
(b) esterificating the compound of formula (V) with α-cyano-3-phenoxy-4-fluoro-benzyl alcohol (IV) in the presence of a weak organic alkali,

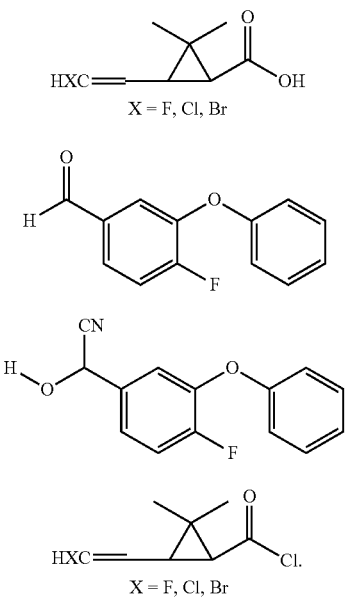

5. The process of claim 4, wherein the weak organic alkali is a tertiary amine such as pyridine, picoline, triethylamine, tripropylamine.

6. An insecticide for controlling or killing vectors in the public hygiene and disease control and insects, nematodes, and acarids parasitizing agricultural animals and plants comprising the compound of claim 1.

7. A method for controlling mosquitoes, cockroaches or houseflies, comprising applying any one of a compound of formula (I), stereoisomers thereof or the mixture of these stereoisomers:

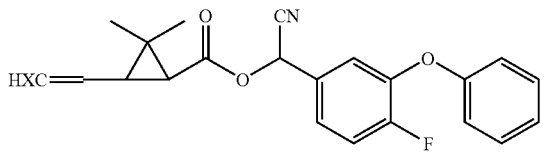

wherein: X represents F, Cl, or Br; or
a compound, stereoisomers thereof or the mixture of these stereoisomers, wherein the compound is selected from the group consisting of:
α-cyano-3-phenoxy-4-fluoro-benzyl-2,2-dimethyl-3-(2-fluorovinyl)cyclopropane carboxylate,
α-cyano-3-phenoxy-4-fluoro-benzyl-2,2-dimethyl-3-(2-chlorovinyl)cyclopropane carboxylate, or
α-cyano-3-pherioxy-4-fluoro-benzyl-2,2-dimethyl-3-(2-bromovinyl)cyclopropane carboxylate.

8. A pesticide composition comprising any one of a compound of formula (I), stereoisomers thereof or the mixture of these stereoisomers:

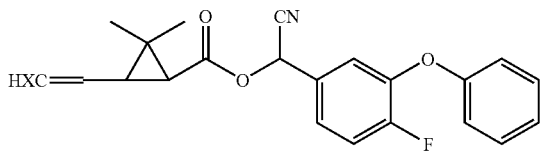

wherein: X represents F, Cl, or Br; or
a compound, stereoisomers thereof or the mixture of these stereoisomers, wherein the compound is selected from the group consisting of:
α-cyano-3-phenoxy-4-fluoro-benzyl-2,2-dimethyl-3-(2-fluorovinyl)cyclopropane carboxylate,
α-cyano-3-phenoxy-4-fluoro-benzyl-2,2-dimethyl-3-(2-chlorovinyl)cyclopropane carboxylate, or
α-cyano-3-phenoxy-4-fluoro-benzyl-2,2-dimethyl-3-(2-bromovinyl)cyclopropane carboxylate,
and an agriculturally acceptably inert carrier.

9. The pesticide composition of claim 8, further comprising a surfactant and/or a solvent.

10. The pesticide composition of claim 8, wherein it is in the form of a powder, a granule, or an emulsion.

11. A process for the preparation of the compound of claim 2, comprising:
(a) condensing the compound of formula (V) with 3-phenoxy-4-fluoro-benzaldehyde of formula (III) in the presence of an alkali metal cyanide by esterification reaction; or
(b) esterificating the compound of formula (V) with α-cyano-3-phenoxy-4-fluoro-benzyl alcohol (IV) in the presence of a weak organic alkali,

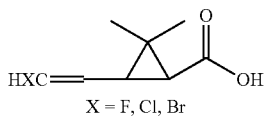

-continued
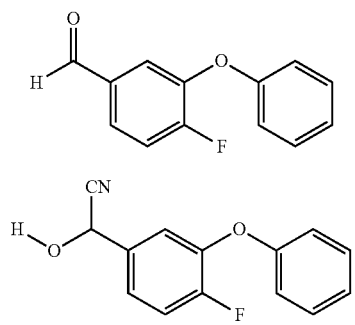
(III)
(IV)
-continued
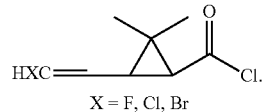
X = F, Cl, Br
(V)
12. The process of claim 11, wherein the weak organic alkali is a tertiary amine such as pyridine, picoline, triethylamine, tripropylamine.
* * * * *